United States Patent
LaHaye

(10) Patent No.: US 8,758,518 B2
(45) Date of Patent: Jun. 24, 2014

(54) APPARATUS AND METHOD FOR CLEANING LUMENS OF MEDICAL DEVICES AND LINES

(76) Inventor: Leon C. LaHaye, Arnaudville, LA (US)

( * ) Notice: Subject to any disclaimer, the term of this patent is extended or adjusted under 35 U.S.C. 154(b) by 381 days.

(21) Appl. No.: 12/440,530

(22) PCT Filed: Sep. 10, 2007

(86) PCT No.: PCT/US2007/019714
§ 371 (c)(1),
(2), (4) Date: Mar. 9, 2009

(87) PCT Pub. No.: WO2008/085209
PCT Pub. Date: Jul. 17, 2008

(65) Prior Publication Data
US 2009/0277478 A1    Nov. 12, 2009

Related U.S. Application Data

(60) Provisional application No. 60/843,296, filed on Sep. 8, 2006.

(51) Int. Cl.
*B08B 7/04* (2006.01)
*B08B 9/00* (2006.01)

(52) U.S. Cl.
USPC ...... 134/18; 134/22.1; 134/22.12; 134/22.18; 134/94.1; 134/166 C; 134/167 C; 134/168 C

(58) Field of Classification Search
USPC ............. 134/18, 22.1, 22.11, 22.12, 93, 94.1, 134/167 C, 169 C, 168 C; 422/28, 93, 292, 422/301
See application file for complete search history.

(56) References Cited

U.S. PATENT DOCUMENTS

| | | | | |
|---|---|---|---|---|
| 4,655,681 A | * | 4/1987 | Mori et al. | 415/100 |
| 5,193,530 A | * | 3/1993 | Gamow et al. | 128/201.27 |
| 5,261,792 A | * | 11/1993 | Schoenmeyr | 417/38 |
| 5,858,305 A | * | 1/1999 | Malchesky | 422/28 |
| 2005/0079094 A1 | * | 4/2005 | Mariotti et al. | 422/3 |

* cited by examiner

*Primary Examiner* — Saeed T Chaudhry
(74) *Attorney, Agent, or Firm* — Lemoine & Associates LLC

(57) ABSTRACT

An apparatus includes a counter top sized outer case; first and second electric motors disposed inside of the case. A positive displacement liquid pump with a pulsating output is operatively connected to said first electric motor and has an input and output port. A positive displacement gas pump with a pulsating output is operatively connected to the second electric motor and has an input and output port. A liquid source is fluidly connected to the input port of the liquid pump. The method further includes connecting a medical line or instrument to be cleaned to the output port of the liquid pump and operating the pump until the line or instrument has been cleaned. The line or instrument is then disconnected and connected to the output line of the gas pump. The gas pump is operated until the line or instrument has been cleared of liquid and then disconnected.

14 Claims, No Drawings

APPARATUS AND METHOD FOR CLEANING LUMENS OF MEDICAL DEVICES AND LINES

CROSS REFERENCE TO RELATED APPLICATIONS

This application relates back and claims priority to U.S. Provisional Patent Application 60/843,296 filed Sep. 8, 2006.

BACKGROUND OF THE INVENTION

1. Field of Invention

In the field of medicine lumens are frequently used for a variety of purposes, including but not necessarily limited to for the purpose of transferring liquids and/or gases through and between various medical equipment and/or to and from the patient. In many instances it is highly desirable that these lumens be cleaned and sterilized for reuse. The invention disclosed herein relates to apparatus and method for cleaning said lumens. With additional particularity the invention herein disclosed relates to apparatus and method for creating a pulsating flow of liquid, typically distilled, sterile water through the lumen of said line, followed by flowing a drying gas, typically sterile filtered air, through said lumen to remove most of said cleaning liquid, prior to sterilization and reuse of said lines.

2. Description of Related Art

Historically medical lumens (of medical lines or instruments) have been cleaned prior to sterilization stream, by flushing them with a syringe containing water. Doing so entails a number of issues, including the cleanliness and sterility of the water used, cleanliness of the syringe used, how large the syringe is, how many times the syringe is used, etc. The process of cleaning medical lumen with syringe is a labor intensive exercise, requiring a fair amount of skill. Each time fluid is pushed through the lumen, the lumen must be disconnected from the syringe, the syringe recharged with fluid, the lumen reconnected to the syringe and another charge of fluid pushed through the lumen. It is generally considered advisable to flush the lumen at least four times in this manner. In as much as that is time consuming and takes a fair amount of skill, it is sometimes not done sufficiently, if at all.

Even if a syringe is used to flush the lumen with liquid there remains the question of removing the liquid prior to sterilization. It has been recognized that if liquid remains in a lumen during attempted sterilization that it may create chambers of air in the lumen which are not adequately sterilized by, for instance, steam. Consequently when a syringe is used to flush a lumen with liquid there remains issues with removing at least sufficient amount of the flushing liquid so that air pockets are not formed in the lumen which prevent adequate sterilization thereof. Sometimes a syringe is used in attempt to push air through the lumen, but that entails a number of issues, including but not limited to size of syringe, number of times it is actually used, whether used properly and quality of air (or other gas) used in the syringe. Attempt may be made to drain the lumen, sometimes by aid of centrifugal force ("slinging" the lumen) to encourage liquid to leave the lumen. This poses its own set of issues, including but not limited to sometimes breaking expensive medical equipment. Sometimes air or other gas (such as oxygen) from a pressurized source may be used. That raises several issues, including whether the gas is oil free, and the expense and fire danger associated with use of pressurized oxygen. Despite all of the problems associated with use of syringes to clean lumens they are still widely used, and used improperly, accounting for increase in rate of complications, such as Toxic Anterior Segment Syndrome ("TASS"), in patients following cataract surgery.

Previous art makes some effort to teach devices other than the traditional, problematic method of using syringes to clean medical lumens prior to sterilization thereof. One such device is seen in U.S. Pat. No. 6,206,014 to Cameron et al. Cameron teaches a counter-top instrument which in sequence automatically delivers liquid then air through a medical line. In order to accomplish said function Cameron utilizes a pressure containing bottle and cap and an electrically driven air-pump. In order to charge the device with fluid the pressure containing cap must be removed from the bottle, water or other liquid poured into the bottle (partially filling it) and the pressure containing cap replace. The air-pump is then used to charge the bottle with pressurized air. Two lines draw from the pressurized bottle. One line draws from the bottom of the bottle and is used to dispense liquid. One line draws from the top of the bottle and is used to dispense air. Each line goes to respective valve (each of which is separately operated by electric signal). After the valves the lines are then connected together and to a lumen to be cleaned. Electric timer is provided to activate the air-pump (to build and maintain desired air pressure in the bottle) and to open and close each valve in proper sequence to dispense liquid through the lumen, then dispense air, then close stop both. The Cameron device poses a number of issues. No easy means is provided to filter (or if filtered, to change the filter when clogged, the air it uses. Each time its bottle is opened to refill it with fluid sterility of the system can be compromised. Some may consider use of pressurized bottle and removable pressure retaining cap to present a safety issue. Alternatively, use of low air pressures limits rate of liquid and air flow through lumens to be cleaned. Cameron does not create a pulsed flow of (high and low velocity) liquid which is believed to be superior cleaning lumens. Use of electric timer, having pre-set times not easily variable reduces flexibility of the device. Lack of foot control requires use of at least one hand to activate the device (or in the event of leakage stop the device) which could be better used to control the lines and instruments being cleaned.

The invention herein disclosed and claimed addresses some of these issues.

OBJECTS OF THE INVENTION

The general object of the invention into provide an improved counter-top instrument, and method of using same, for cleaning the lumens of medical lines and equipment prior to sterilization and reuse. With more particularity an object of the invention is to provide apparatus and method for flowing a pulsating flow of rinsing liquid, usually sterile distilled water, then a drying gas through medical equipment and lines prior to sterilization and reuse. Other objects of the invention relate to providing means to draw (if desired) sterile, non-pyrogenic, particulate free liquid from a wide variety of non-pressurized (rigid or flexible) containers, provide both sterile liquid and gas, provision of foot control so that both hands are free to control the medical lines and equipment during rinsing, provide unlimited volumes of liquid and gas and change direction of flow if desired.

SUMMARY OF THE INVENTION

The apparatus set forth herein is mounted in a case and is designed for compact counter top operation. The case houses the complete electrical system, power mechanisms, and controls to provide for operation of a self priming liquid pump with pulsating output, such as rotary peristaltic pump, and for a gas, which may be a diaphragm type pump for the delivery of gas. Either input, output or both of gas pump may be filtered to sub-micron level (0.2 micron pore filters, which may be used, are considered as blocking passage of all airborne bacteria). Liquid may be drawn from virtually any rigid or flexible container. Pump head of peristaltic pump may be protected by transparent door and safety switch cooperatively engaged with door. Direction of liquid flow may be reversed by either reversing the direction of rotation of the peristaltic pump or by reversing lines attached to suction or discharge of pump. Foot controls may be provided for actual dispensing of fluid and/or gas.

PREFERRED EMBODIMENT OF THE INVENTION

While the present invention will be described with reference to preferred embodiments, it will be understood by those who are skilled in the art that various changes may be made and equivalents may be substituted for elements thereof without departing from the scope of the invention. In addition, many modifications may be made to adapt a particular situation or material to the teachings of the invention without departing from the essential scope thereof. It is therefore intended that the present invention not be limited to the particular embodiments disclosed as the best mode contemplated for carrying out this invention, but that the invention will include all embodiments and legal equivalents thereof.

In preferred embodiment the apparatus herein disclosed is mounted in a strong, compact case suitable for counter-top operation. The apparatus includes a peristaltic pump driven by electric motor for dispensing fluids (which fluid will typically be sterile distilled water) and a gas pump, preferably a diaphragm type pump driven by electric motor for dispensing drying gas, which will preferably be highlyfiltered (sub-micron) air. In preferred embodiment of the invention said case will have a front panel which includes the controls frequently used, a door which allows threading of a flexible tube through the channel of a peristaltic pump and a fitting through which pressurized gas, usually air is delivered. Those skilled in the art will realize these components could be mounted on top, sides or some other place on the case which provides the user to conveniently operate hand operable controls, connect and disconnect lines to input and output of the peristaltic pump and connect and disconnect lines to pressurized gas. All such embodiments are intended to be considered part of the invention herein disclosed and claimed.

In preferred embodiment a first electric control switch is located on the front panel of the case. In the preferred embodiment of the invention this first switch will have two positions, one of which disarms the electric motors of the invention from operating, and the other position which arms them to be operated by foot control. In another embodiment of the invention this first switch may also have a third. "manual" position, namely a position which by-passes the foot control, causing a selected motor to operate regardless of whether the foot control (a preferred component of the invention) is activated or not. If manual position is provided it is preferable to use spring loaded to "off" (or inoperative) type switch; but need not necessarily be, all embodiments of switching arrangements apparent to those skilled in the art are intended to be considered part of the invention herein disclosed and claimed.

Other electric controls of the preferred embodiment of the invention may include appropriately mounted (preferably on the front panel of the case) second, third, or more switches, including: an electric control to select gas or liquid, a control to select different speed of one or both electric motors (if electric motors of variable speed are provided), a control to reverse direction of electric motors (if reversible electric motors are provided) and a foot control for "normal" operation of the selected liquid or gas pump (thereby freeing both hand of the user to handle the line or instrument to be cleaned, in particular direct the flow of liquid into container for collection and proper disposal). The foot control will preferably be removably connected to the side or rear of the case so that the wires from the case to the foot control (so that they do not become entangled with the lines to be cleaned, which will typically be handled in front of the case).

In the preferred embodiment of the invention a peristaltic pump driven by electric motor is the preferred means for pumping liquid, typically clean, sterile, non-pyrogenic, distilled or de-ionized water, through the lumens of medical devices and lines to be cleaned. Other positive displacement pumps which do not require lubrication, have seals or rings that might leak and have a pulsating output pressure be also used. In the preferred embodiment of the invention the head of the peristaltic pump is mounted vertically and extends through the front face of the case to allow easy threading of a flexible tube through the channel of the peristaltic pump. In addition thereto in the preferred embodiment of the invention the input and output ports of the peristaltic pump will be oriented facing away from the controls of the device so that lines going to an from the peristaltic pump do not obstruct the operators access to said controls.

In addition thereto in the preferred embodiment a door to access the track of the peristaltic pump through which tubing is threaded will be provided on the front panel of the case. As a safety feature a "cut off", electrically disabling the electric motor of the peristaltic pump from operating if said door is open, so as to mitigate against the possibility of injury to fingers when threading a flexible tube through the channel of the peristaltic pump. In preferred embodiment the door will be comprised of a transparent material so that operation of the pump mechanism, and condition of the tubing passing therethrough, may be observed.

It should be noted at this point that reversal of liquid flow may be easily achieved in a variety of ways, including but not necessarily limited to reversing rotation of the peristaltic pump motor by simply reversing which port (input or output) of the peristaltic pump the lumen or instrument to be cleaned is connected to.

In the preferred embodiment of the invention a diaphragm pump driven by electric motor is the preferred means for pumping gas, typically oil-free, filtered air, through the lumens of medical devices and lines to be cleaned. Other positive displacement pumps which do not require lubrication, have seals or rings that might leak and have a pulsating output pressure be also used. In the preferred embodiment of the invention the front panel will contain a fitting forgas (typically air) input to the pump and one for gas (typically air) output from said pump. In preferred embodiment either the input fitting, the output fitting or both will be adapted to receive a gas filter. In preferred embodiment said filter will remove particulate matter, biological or otherwise, as small as 0.2 microns in size, thereby gas (preferably air) used to dry the lumen or instrument to be dried will be sterile or nearly so.

The described apparatus provides user options of either delivering fluids to the tubing, instrument, or device to be rinsed from a fluid source or aspirating fluids from a fluid source through the tubing, instrument or device to be rinsed.

To deliver fluids from a fluid source to the tubing, device or instrument to be rinsed the end of fluid delivery tubing from the suction side of the peristaltic pump is placed into the source fluid. Typically said fluid will be clean, sterile, non-pyrogenic water. After placing suction tubing in a source of fluid the device, tubing or instrument to be rinsed is connected to the opposite (pressure) side of the peristaltic pump. Next the user selects the flow rate ("high" of "low") which is desired. Use of "low" flow rate may be necessary for small, or obstructed lumen or instrument. Next the other end of the instrument, tubing, or device to be rinsed should be placed over some sort of catch or disposal container or drain. Alternatively, if permitted, fluid from the instrument, tubing or device to be rinsed may be returned, by tubing, to the source container for multiple passage through said instrument, tubing or device. Finally, In preferred embodiment, a foot control (or alternatively manual switch, which manual switch may be connected to timer) is used to activate the peristaltic pump for a desired duration of time or until desired condition of the instrument, tubing or device is achieved. After completion of rinse the electric motor of the peristaltic pump is de-energized.

Following rinsing with fluid the tubing, device or instrument may be dried by gas (which will typically be sub-micron filtered air). To do so the instrument, tubing, or device through which gas will be flowed will generally be placed over a sink or other type of catch basin or drain so that the fluid blown from the instrument, tubing or device being cleaned is properly disposed off. If desired air exiting from said instrument, tubing or device may be captured in a container and/or exhausted by hood or other type of gas removal device. Next the gas delivery function is enabled by switch on the front panel of the case. Finally, in the preferred embodiment of the invention, air is actually dispensed (electric motor of the gas pump is activated) by either foot control or manual switch, which may be connected to timer.

While the above description contains certain specifics, these should not be construed as limitations on the scope of the invention, but rather as an exemplification of one preferred embodiment thereof. Accordingly, the scope of the present invention should be determined not by the embodiment(s) illustrated, but by the claims and their legal equivalents as may later be granted upon this or related patent applications.

The invention claimed is:

1. An apparatus for cleaning medical lines and instruments comprising:
   a. a counter top sized outer case having a front panel;
   b. a first electric motor disposed inside of said case;
   c. a second electric motor disposed inside of said case;
   d. operatively connected to said first electric motor an oil-less, seal-less, ring-less positive displacement liquid pump which has a pulsating output and having a vertically disposed head extending outside of said case;
   e. input and output port operatively connected to said liquid pump;
   f. operatively connected to said second electric motor an oil-less, seal-less, ring-less positive displacement gas pump which has a pulsating output;
   g. input and output port operatively connected to said gas pump; and,
   h. a first electric switch disposed on said front face of said case and a second electric switch disposed on said front panel of said case, wherein said first switch is selectively operable between a first, second and third position, wherein in said first position electric power is not permitted to pass through said first electric switch, in said second position electric power is permitted to pass to said second electric switch, in said third position electric power is allowed to pass to a foot operated switch which is operably connected to said second electric switch and said second electric switch is selectively operable between a first and a second position wherein in said first position electric power is permitted to flow through said second switch to said first electric motor and in said second position electric power is permitted to flow through said second switch to said second electric motor.

2. The apparatus of claim 1 wherein said liquid pump is a peristaltic pump.

3. The apparatus of claim 2 wherein said gas pump is a peristaltic pump.

4. The apparatus of claim 3 wherein said head of said peristaltic pump further comprises a door operatively connected to an electric switch which will not permit electric power to flow to said peristaltic pump unless said door is closed.

5. The apparatus of claim 2 wherein said gas pump is a diaphragm pump.

6. The apparatus of claim 2 wherein said head of said peristaltic pump further comprises a door operatively connected to an electric switch which will not permit electric power to flow to said peristaltic pump unless said door is closed.

7. The apparatus of claim 1 wherein said liquid pump is a diaphragm pump.

8. The apparatus of claim 7 wherein said gas pump is a peristaltic pump.

9. The apparatus of claim 8 wherein said head of said peristaltic pump further comprises a door operatively connected to an electric switch which will not permit electric power to flow to said peristaltic pump unless said door is closed.

10. The apparatus of claim 7 wherein said gas pump is a diaphragm pump.

11. The apparatus of claim 1 wherein said gas pump is a peristaltic pump.

12. The apparatus of claim 11 wherein said head of said peristaltic pump further comprises a door operatively connected to an electric switch which will not permit electric power to flow to said peristaltic pump unless said door is closed.

13. The apparatus of claim 1 wherein said gas pump is a diaphragm pump.

14. A method for cleaning medical lines and instruments comprising the steps of:
   a. providing an apparatus comprising a counter top sized outer case having a front panel; a first electric motor disposed inside of said case; a second electric motor disposed inside of said case; operatively connected to said first electric motor an oil-less, seal-less, ring-less positive displacement liquid pump which has a pulsating output and having a vertically disposed head extending outside of said case; input and output port operatively connected to said liquid pump; operatively connected to said second electric motor an oil-less, seal-less, ring-less positive displacement gas pump which has a pulsating output; input and output port operatively connected to said gas pump; and, a first electric switch disposed on said front face of said case and a second electric switch disposed on said front panel of said case, wherein said first switch is selectively operable between a first, second and third position, wherein in said first position electric power is not permitted to pass through said first electric switch, in said second position electric power is permitted to pass to said second electric switch, in said third position electric power is allowed to pass to a foot operated switch which is operably connected to said second electric switch and said second electric switch is selectively operable between a first and a second position wherein in said first position electric power is permitted to flow through said second switch to said first electric motor and in said second position electric power is permitted to flow through said second switch to said second electric motor:

b. providing a liquid source;

c. fluidly connecting said liquid source to the input port of said liquid pump;

d. fluidly connecting the medical line or instrument to be cleaned to the output port of said liquid pump;

e. selectively operating said first, said second and said foot operated electric switches so as to cause said liquid pump to operate by foot control until the medical line or instrument to be cleaned is determined to be sufficiently cleaned;

f. disconnecting said the medical line or instrument from the output port of said liquid pump and connecting said medical line or instrument to the output port of said gas pump;

g. selectively operating said first, said second and said foot operated electric switches so as to cause said gas pump to operate by foot control until the medical line or instrument to be cleaned is determined to be sufficiently cleared of liquid; and, h. disconnecting said the medical line or instrument from the output port of said gas pump.

* * * * *